United States Patent
Habermehl et al.

(10) Patent No.: US 8,698,778 B2
(45) Date of Patent: Apr. 15, 2014

(54) METHOD OF MANIPULATING IMPEDANCE PLANE WITH A MULTI-POINT TOUCH ON TOUCH SCREEN

(75) Inventors: Jason Habermehl, Québec (CA); Benoit Lepage, Québec (CA); Tommy Bourgelas, Québec (CA)

(73) Assignee: Olympus NDT, Waltham, MA (US)

(*) Notice: Subject to any disclaimer, the term of this patent is extended or adjusted under 35 U.S.C. 154(b) by 122 days.

(21) Appl. No.: 13/561,333

(22) Filed: Jul. 30, 2012

(65) Prior Publication Data

US 2014/0028608 A1     Jan. 30, 2014

(51) Int. Cl.
*G06F 3/045*     (2006.01)
(52) U.S. Cl.
USPC .......................................................... 345/174
(58) Field of Classification Search
CPC ..................................................... G06F 3/045
USPC .......................................................... 345/174
See application file for complete search history.

(56) References Cited

U.S. PATENT DOCUMENTS

| | | | |
|---|---|---|---|
| 2011/0050627 A1* | 3/2011 | Liao et al. | 345/174 |
| 2011/0096017 A1* | 4/2011 | Li et al. | 345/174 |
| 2011/0216035 A1* | 9/2011 | Shih et al. | 345/174 |
| 2011/0227870 A1* | 9/2011 | Kim | 345/174 |
| 2012/0026133 A1* | 2/2012 | Rofougaran | 345/174 |
| 2012/0050204 A1* | 3/2012 | Kao et al. | 345/174 |
| 2012/0050205 A1* | 3/2012 | Kao et al. | 345/174 |
| 2012/0092296 A1* | 4/2012 | Yanase et al. | 345/174 |

* cited by examiner

*Primary Examiner* — Fred Tzeng
(74) *Attorney, Agent, or Firm* — Ostrolenk Faber LLP

(57) ABSTRACT

A touch screen is disclosed which responds to a user's touch for re-drawing, re-scaling, re-translating and re-positioning an impedance plane signal received from non-destructive testing equipment, such as an eddy current sensor. The impedance plane is manipulated by slidingne, two or more fingers simultaneously to an end position to effectuate a complete re-drawing operation of the image.

22 Claims, 16 Drawing Sheets

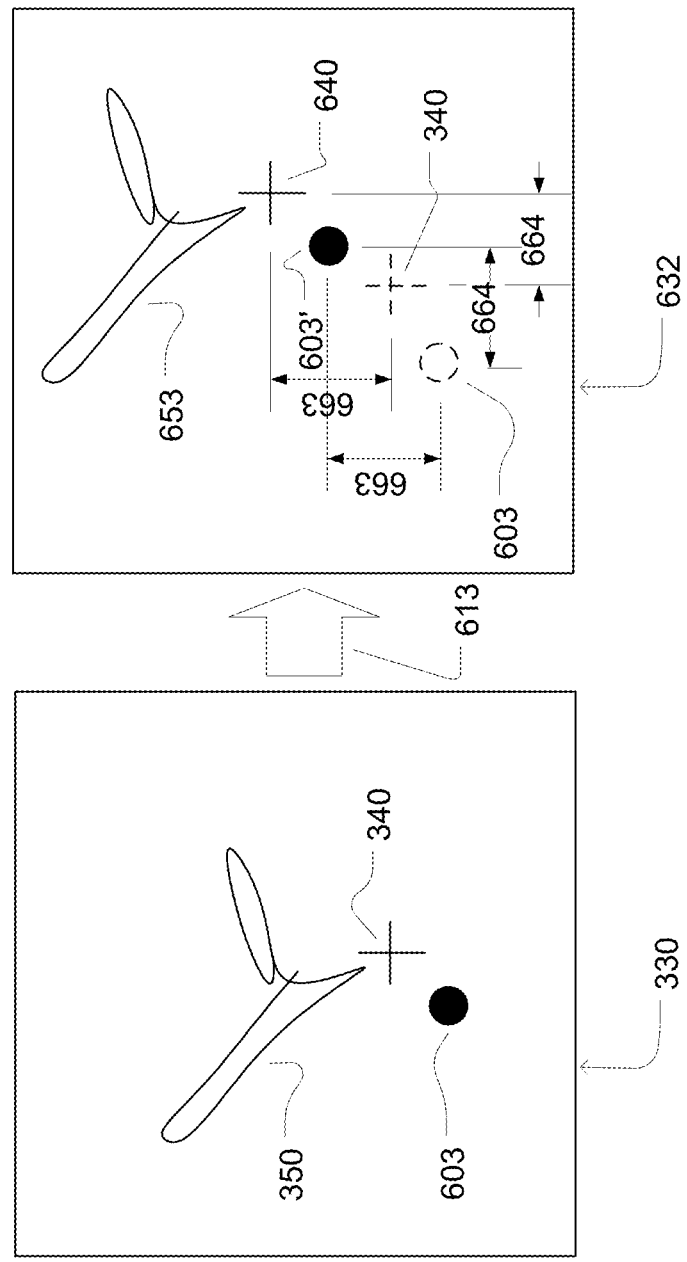

METHOD OF MANIPULATING IMPEDANCE PLANE WITH A MULTI-POINT TOUCH ON TOUCH SCREEN

FIELD OF THE INVENTION

The present invention relates to non-destructive testing and inspection systems (NDT/NDI), using more specifically Eddy Current Technology (ECT), Eddy Current Array technology (ECA), Pitch-Catch Bond Testing (PCBT) and Resonance Bond-Testing (RBT).

BACKGROUND OF THE INVENTION

Eddy current inspection is commonly used as non-destructive control to detect flaws in surfaces of manufactured components fabricated from a conductive material, such as bars, tubes, and special parts for the automotive, aeronautic or energy industries.

Since the 1950's, eddy current instruments render test information on an impedance plane display. The original concept of the impedance plane display was to divide the detector coil impedance into resistive and reactive components to produce bi-dimensional figures yielding significant information on the inspected component. The concept quickly evolved as users understood the value of manipulating the impedance plane to highlight specific features of the component to be tested.

Portable eddy current instruments now offer many controls to achieve these impedance plane manipulations, including: gain, rotation, horizontal position, vertical position, horizontal gain and vertical gain. All controls are typically accessible in various instrument menus and are iteratively applied by the instrument user to produce the desired impedance plane setup. This operation can become time consuming as the user needs to go through the whole sequence before each new inspection procedure (sometimes twice for a dual frequency setup). Thus, there is a need for an easier and faster way to manipulate the impedance plane on NDT equipment, such as a portable eddy current instrument.

Another limitation of the current method is the troublesome interaction between some parameters such as vertical gain and rotation, which require some additional care when instruments settings are defined.

More specifically, some additional drawbacks involved in a typical prior art portable eddy current instrument featuring an eddy current impedance plane that shows signal produced by scanning a defect with a probe and the controls available for manipulating this impedance plane signal to enhance the detectability of defect signal over noise signal, are as follows. These controls typically involve the use of multiple buttons associated with multiple parameters displayed on the instrument screen. Parameters found on most eddy current instruments include impedance plane rotation angle, gain, horizontal gain, vertical gain and settings to configure the horizontal and vertical position of the null point. The parameters for impedance plane manipulation are sometimes located in various sub-menus of the instrument. The values for each parameter are typically modified with a knob or by using a keypad.

An inspection procedure typically describes the desirable signal shapes on a reference block in order to obtain a reliable and repeatable inspection. Those procedures typically require setting the noise signal on the horizontal axis and defines the other parameters to maximize the detectability of defect signal on the vertical axis in order to decouple the defect and noise signals. Furthermore, since eddy current parameters are closely related to probe selection, inspection condition and target defects, those parameters must be set before any inspection task.

The original impedance plane signal is iteratively modified to highlight the defect signal with the prior art method. Consecutive steps typically include gain adjustment, signal rotation, vertical gain adjustment, vertical movement of the null point and horizontal movement 14 of the null point. Those operations are often conducted on live data (in this case the user needs to repeatedly scan the defect area) or on paused (frozen) data. In the latter case, some post processing is used to manipulate the data previously acquired to reflect in real time changes made on the original signal. For purposes of illustration, the figures and descriptions provided herein are more oriented toward frozen data style manipulation.

Multi-point touch screen displays now available on the market make it possible for users to directly interface with instruments without going through menus and sub-menus. This invention provide means to benefit from a multi-point touch screen to provide new ways to manipulate an impedance plane and to circumvent current limitations of prior art methods.

An object of the invention is to reduce the number of steps required for the controls so as to produce an equivalent end result and thus to increase productivity.

Another object is to provide a simplified and more intuitive operation which, in turn, provides an enhanced user experience.

SUMMARY OF THE INVENTION

The invention is a multi-point touch screen apparatus, system, means and a method of using the same in order to manipulate an eddy current impedance plane signal. The invention make it possible conduct substantially all required impedance plane manipulations in fewer steps while providing a more intuitive interaction as the user can be empowered with the feeling that he or she is actually controlling or adjusting the signals directly with his or her hand.

Other features and advantages of the present invention will become apparent from the following description of the invention, which refers to the accompanying Drawings.

With reference to the Drawings, the features thereof are described below.

DETAILED DESCRIPTION OF THE INVENTION

Figure 1:
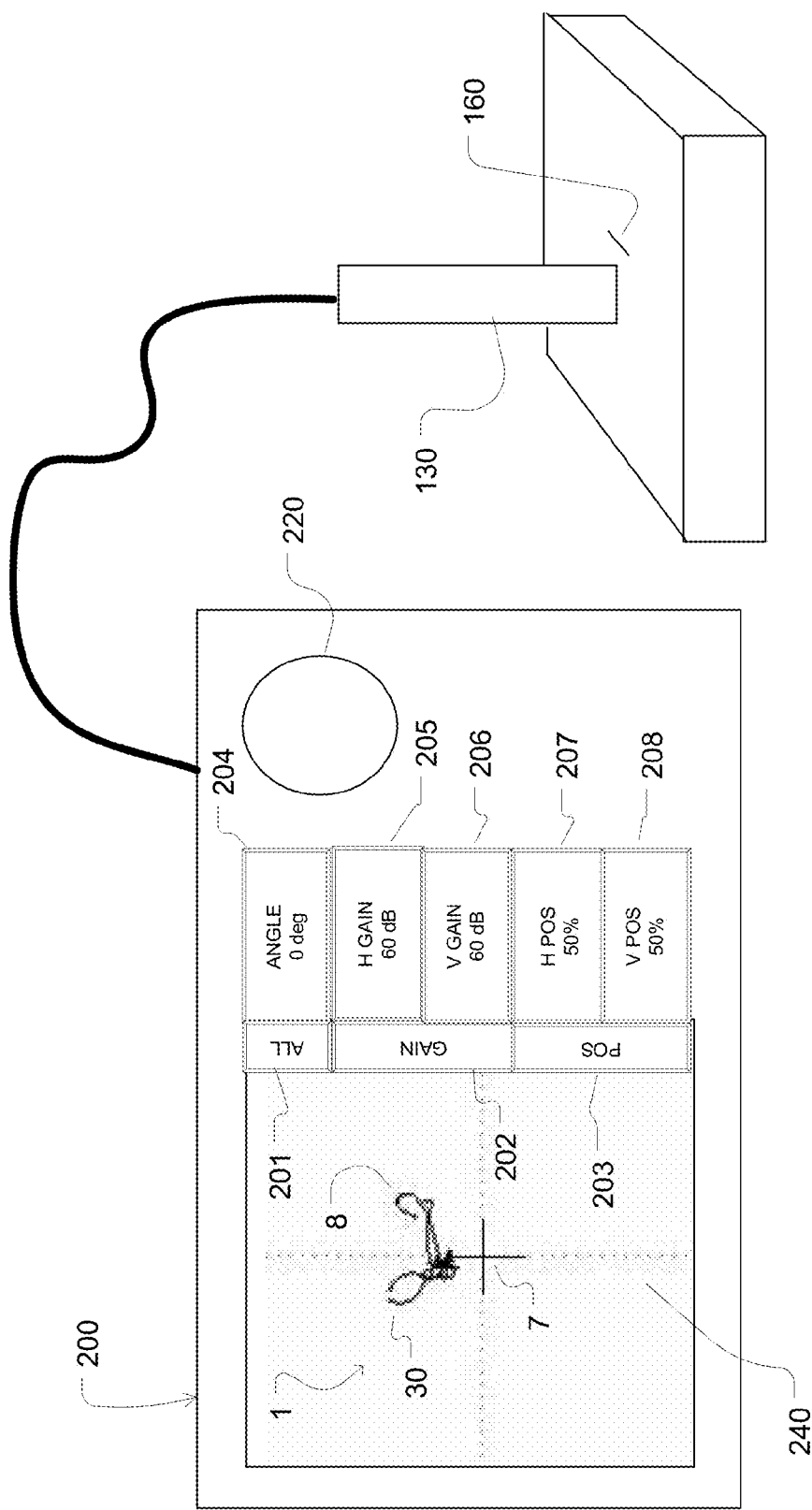
FIG. 1 is a schematic depiction of an eddy current instrument built in accordance with the teaching of the invention.

FIG. 1 is a first overview of an instrument 200 built in accordance with an aspect of teachings of this invention using a multi-point touch screen interface 240 and displaying the impedance plane 1 for representing the impedance plane signal 8 and displaying a set of buttons 201, 202, 203, 204, 205, 206, 207 and 208.

A benefit of the use of a touch screen is the integration of the buttons and displayed parameters to provide the user with a set of buttons 201, 202, 203, 204, 205, 206, 207 and 208. According to an aspect of the invention, a touch screen interface provides the user with the ability to manipulate impedance plane signal 8 without using knob 220 (although 220 can still be used for some precise operations). They may also have ability to modify simultaneously many parameters of the impedance plane with a single touch screen operation.

Figure 2A:
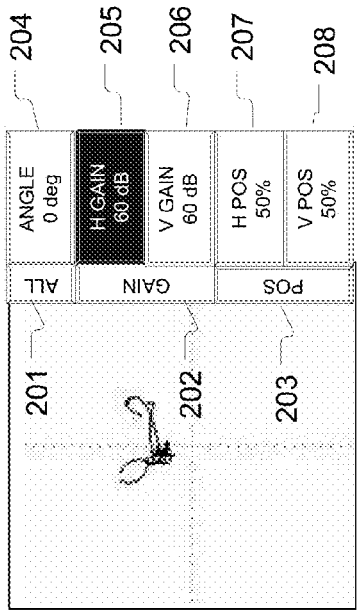
FIG. 2 illustrates various possibilities regarding parameter selection through the use of a touch screen interface according to an aspect of the invention.

FIG. 2a shows how parameters to be modified are first selected on the touch screen interface. Buttons 204 (rotation angle), 205 (horizontal gain), 206 (vertical gain), 207 (horizontal position) and 208 (vertical position) refer to individual parameters. Selecting one such parameter on the touch screen, as seen in FIG. 2a, makes it possible to modify these values on touch screen interface 240 or with knob 220. Now looking at FIG. 2b, selecting button 202 (gain) simultaneously activates buttons 205 and 206 and makes it possible to modify both values on touch screen 240 or with knob 220. Similar results can be achieved with button 203 (null point position) which activates 207 and 208 except that combined position 207 and 208 can only be modified using the touch screen interface 240. Preferably, as shown in FIG. 2c button 201 may be provided to allow a user to select all parameters simultaneously in order to benefit fully from the touch screen operation. For the touch screen operation, it is also possible to combine any selection of parameters as shown in FIG. 2d, where 202 and 204 have been selected.

Figure 14:
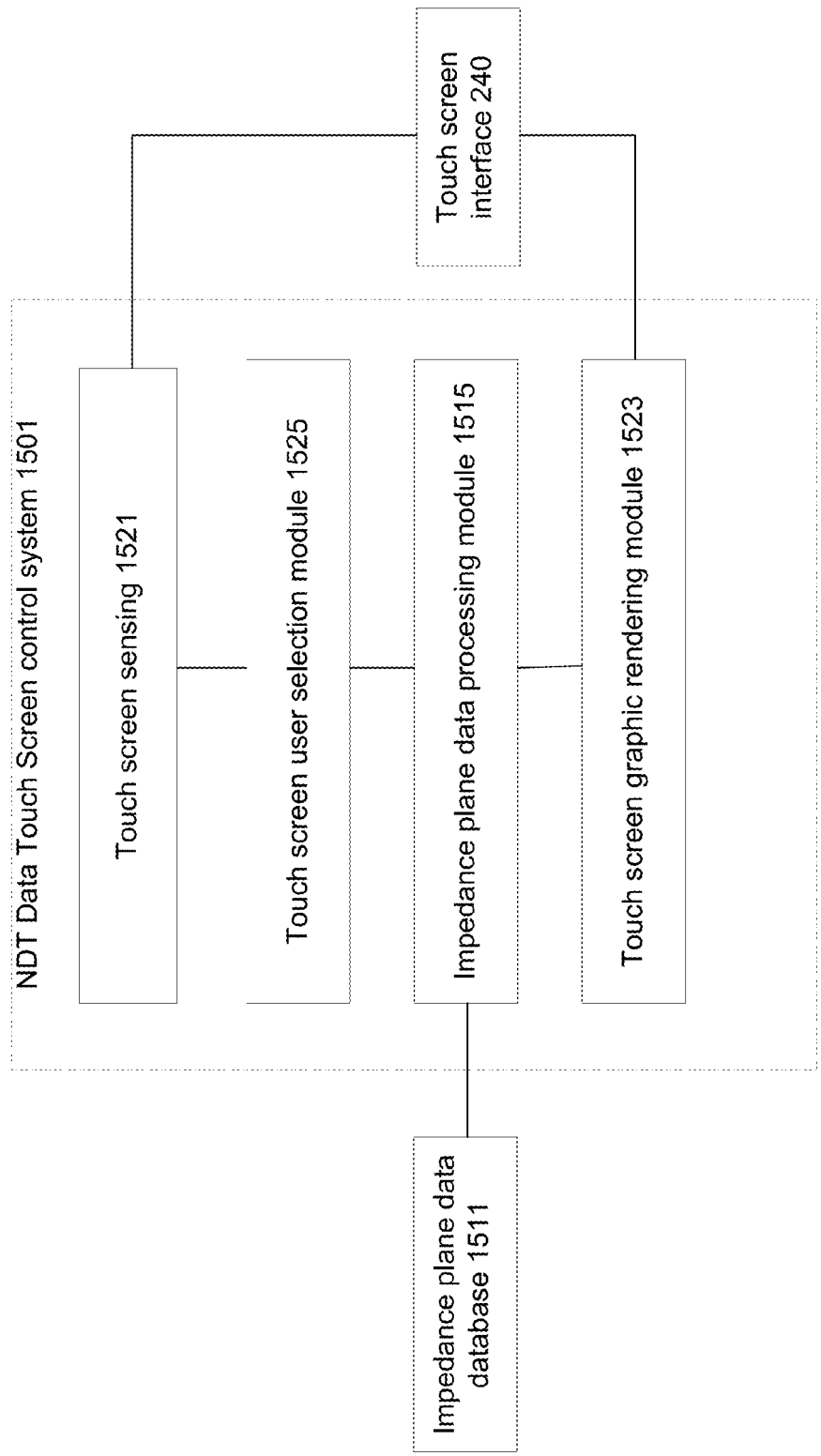
FIG. 14 is a block diagram showing components of a Non-Destructive Instrument Data Touch Screen Engine, according to an aspect of the invention.

Reference is now made to FIG. 14 presenting the forgoing description with an overall context within a Non-Destructive Data Touch Screen system 1501. The NDT signal data, such as from an eddy current probe, are gathered in an impedance plane data database 1511. Based on this data, impedance plane data processing module 1515 provides information to touch screen graphic rendering module 1523 sufficient to draw an image representing the impedance plane signal on touch screen 240.

Touch screen sensing 1521 signals to touch screen user selection module 1525 that the user has touched using one or more fingers, or using other parts of his hand, the touch screen interface 240. That is, touch screen user selection module 1525 detects what user's selection of the parameter and gives a context for the subsequent touch screen input, then transmits such touch input to impedance plane data processing module 1515 the coordinates, direction, pattern and/or timing of the touch of the user. Based on this information, impedance plane data processing module 1515 transmits instructions to touch screen graphic rendering module 1523 to redraw the image of the impedance plane signal on touch screen interface 240 based on the user's touch.

Figure 3:
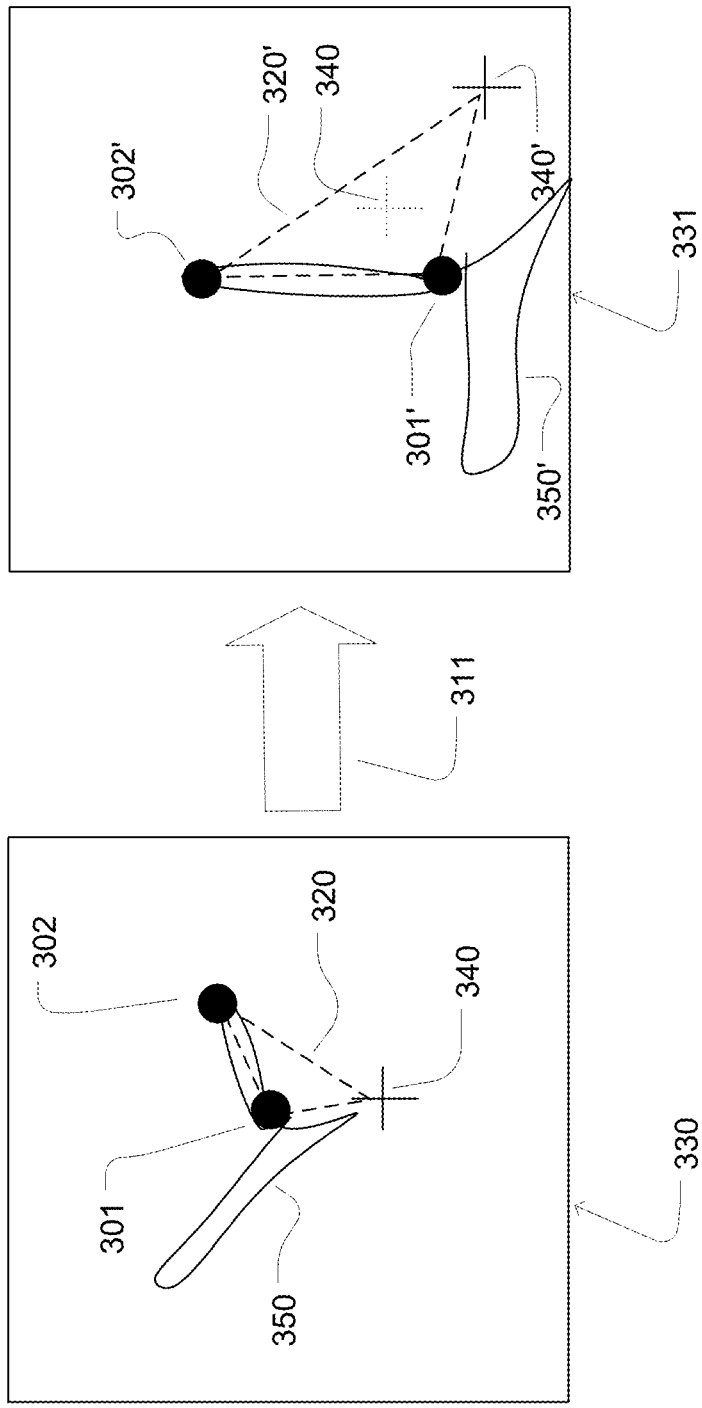
FIG. 3 illustrates a basic process behind the impedance plane signal's manipulations using the touch screen interface according to an aspect of the invention.

In order to understand principles underlying an aspect of the invention, first consider the case where all parameters are selected (step 1102 in FIG. 8) and where horizontal and vertical gains 205 and 206 have the same value. In this case, as shown on FIG. 3 and FIG. 8 the impedance plane 330 and corresponding impedance plane signal 350 is modified by pressing and holding two point contacts 301 and 302 to their final position 301' and 302' (step 1106).

The whole impedance plane is morphed (scaled, translated and rotated) (step 1108) in order to keep the triangle 320 (defined by 301, 302 and 340) shape constant with the position of contact points 301' and 302'. As part of the process, the new position of null point 340' is defined and the information previously located under 301 and 302 is now under 301' and 302'. A preview of the modified impedance plane 331 is constantly displayed to the user (step 1109). Once the user obtains the desired signal 350' and removes his fingers from the touch screen, the modified instrument parameters 204, 205, 206, 207 and 208 are applied (step 1112) to the instrument and impedance plane 331 is displayed (step 1114).

Figure 4:
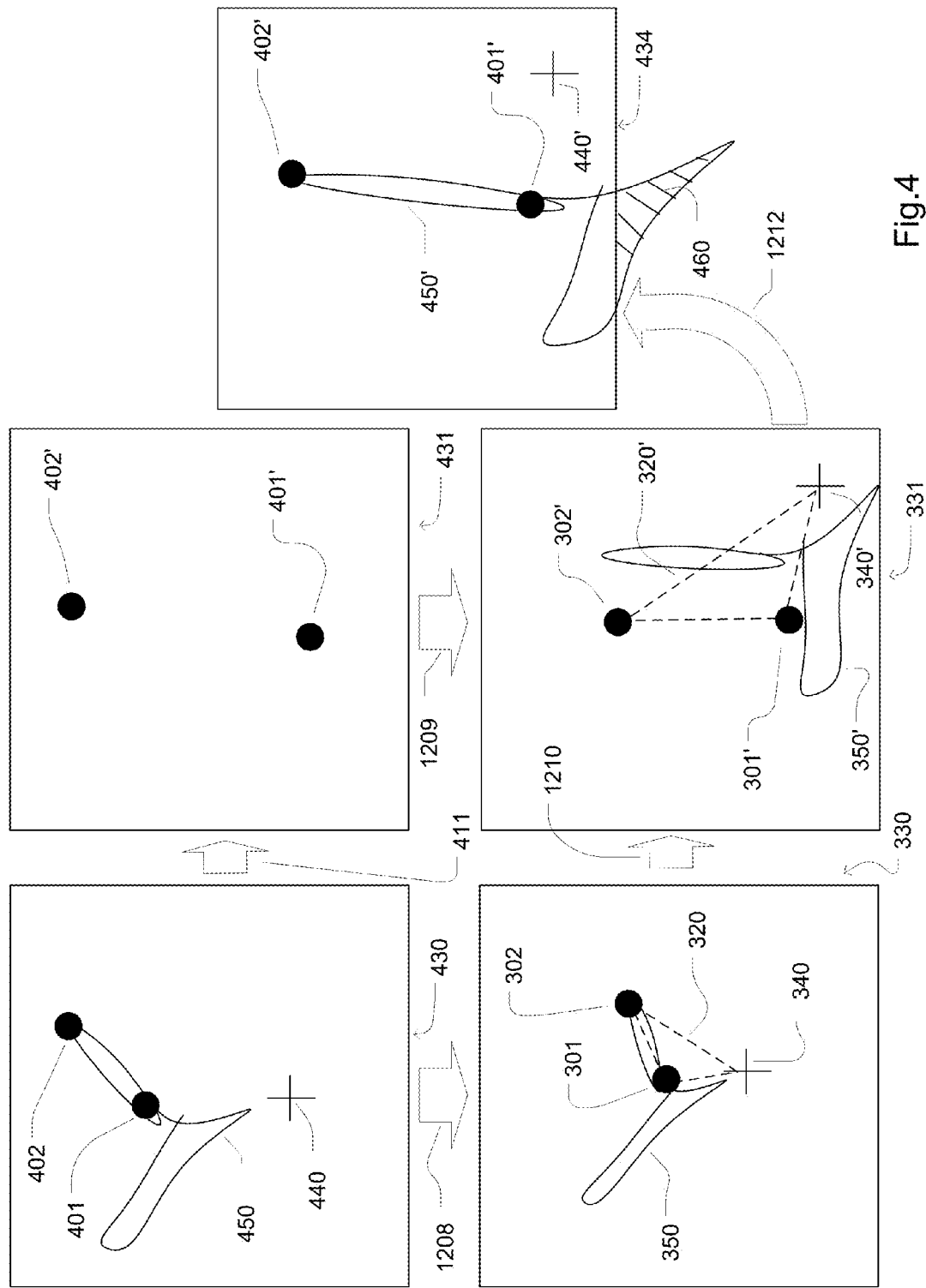
FIG. 4 illustrates a manipulation of the impedance plane when horizontal and vertical gains are different according to an aspect of the invention.
Figure 9:
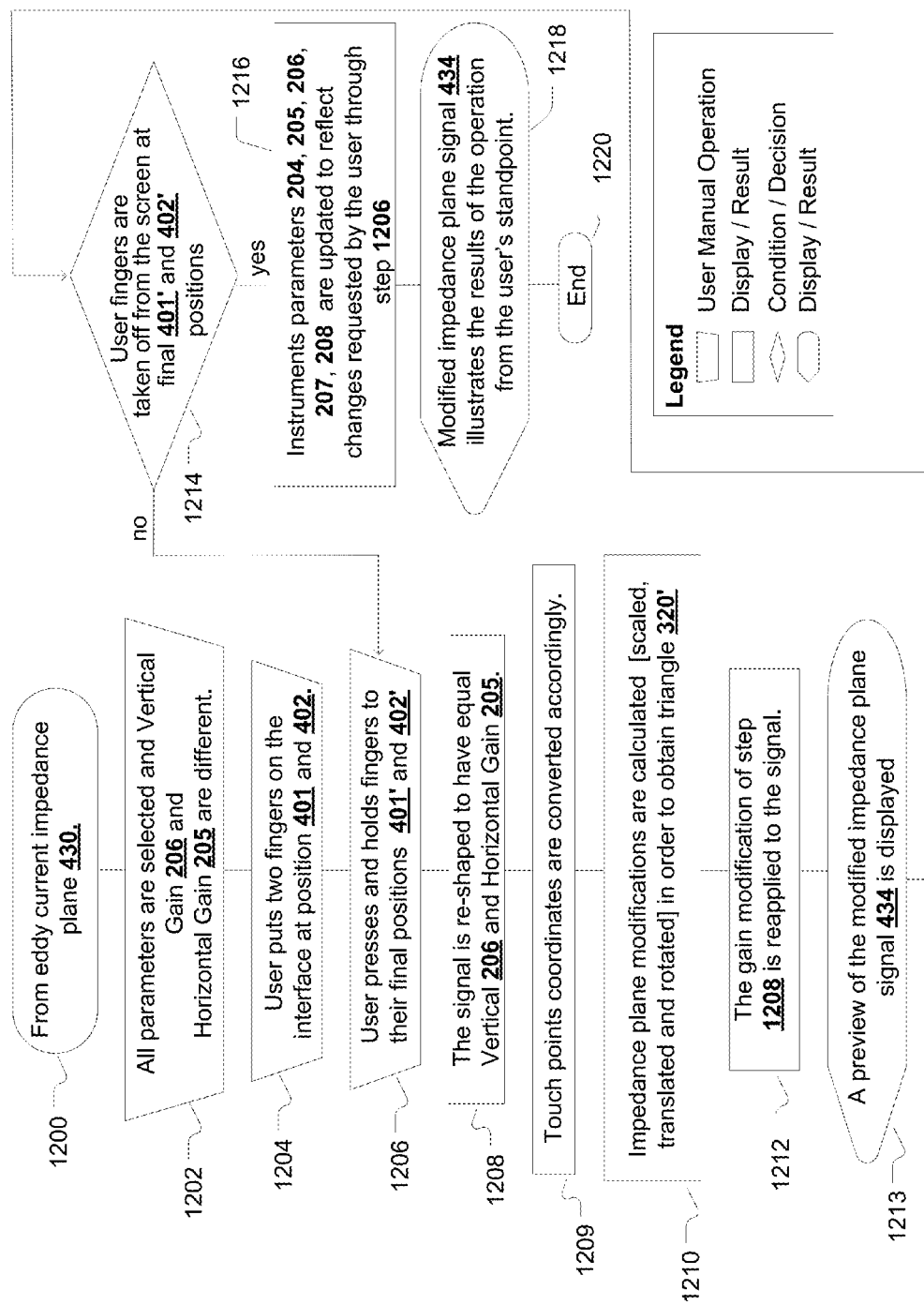
FIG. 9 is a flow diagram illustrating the operation illustrated in FIG. 4 according to an aspect of the invention.

Now a more complex situation is considered as illustrated in FIG. 4 and FIG. 9, where the vertical gain and horizontal gain are different. In this case, the vertical gain is superior by 6 dB, but the explanation and concepts described here are applicable for any gain configuration. At the beginning of the process, the original impedance plane signal 450 is selected at positions 401 and 402 and moved to 401' and 402' (step 1206). To evaluate the impact of touch screen operation 411 on signal 450, a first step 1208 is made to remove the gain difference on the various features of 430 to get impedance plane 330, signal 350 and contact position 301 and 302.

Then, the new contact positions 401' and 402' are processed through step 1209 to remove the gain difference in order to obtain new contact positions 301' and 302' on impedance plane 331.

Figure 8:
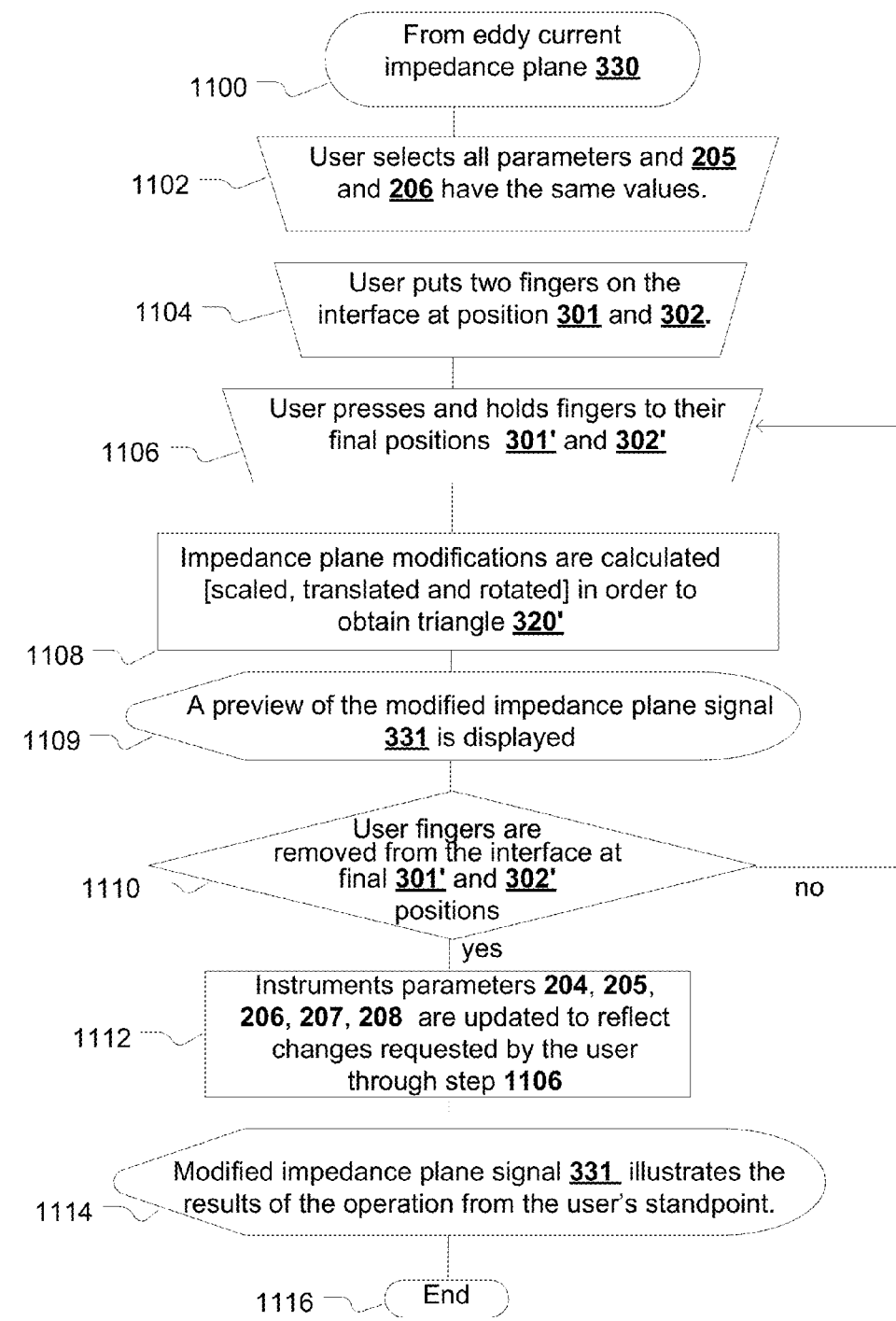
FIG. 8 is a flow diagram illustrating the operation illustrated in FIG. 3 according to an aspect of the invention.

Because the gain difference have been removed in previous steps 1208 and 1209, Step 1210 which makes it possible to calculate signal 350' and null position 340' on the impedance plane 331 is the same way as step 1108 previously described in FIG. 8. We now complete the process by applying back the gain difference (in this case +6 dB on the vertical axis) in step 1212. The resulting impedance plane 434 provides the user with morphed signal 450' and updated null position 440' (step 1213). Note that in this case a portion 460 of 450' is out of 434 and is thus removed from the information displayed to the user. Once the user obtains the desired signal and removes his fingers from the touch screen, the modified instrument parameters 204, 205, 206, 207 and 208 are applied (step 1216) to the instrument and the whole impedance plane 434 is displayed (step 1218). Steps 1208, 1209 and 1210 can be performed automatically by the system.

Figure 2B:
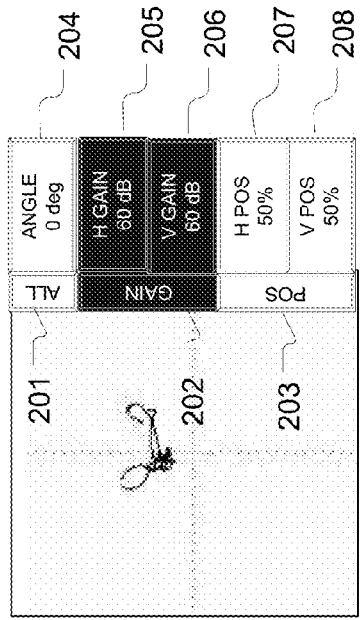
Figure 2C:
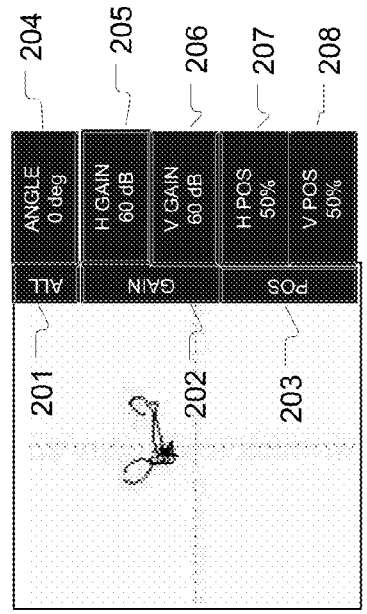
Figure 2D:
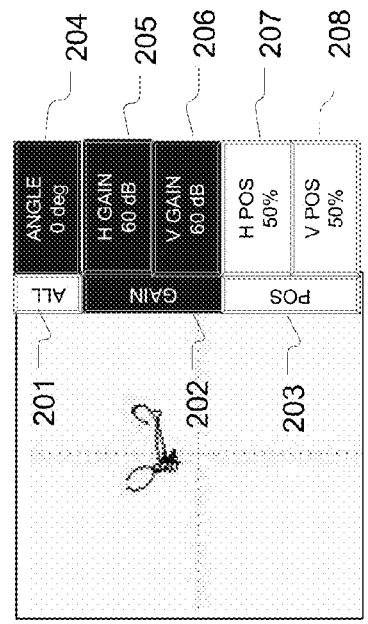
Figure 5:
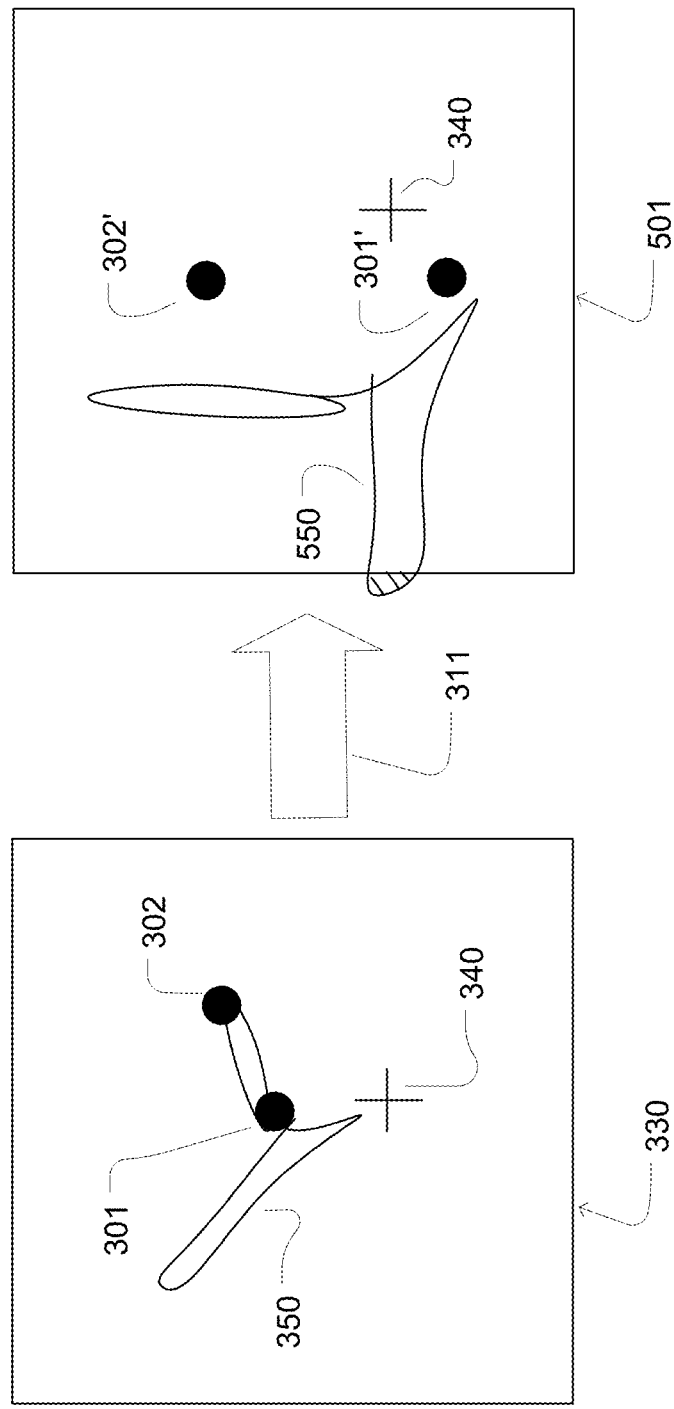
FIG. 5 illustrates how the impedance plane is manipulated when some parameters are fixed according to an aspect of the invention.
Figure 10:
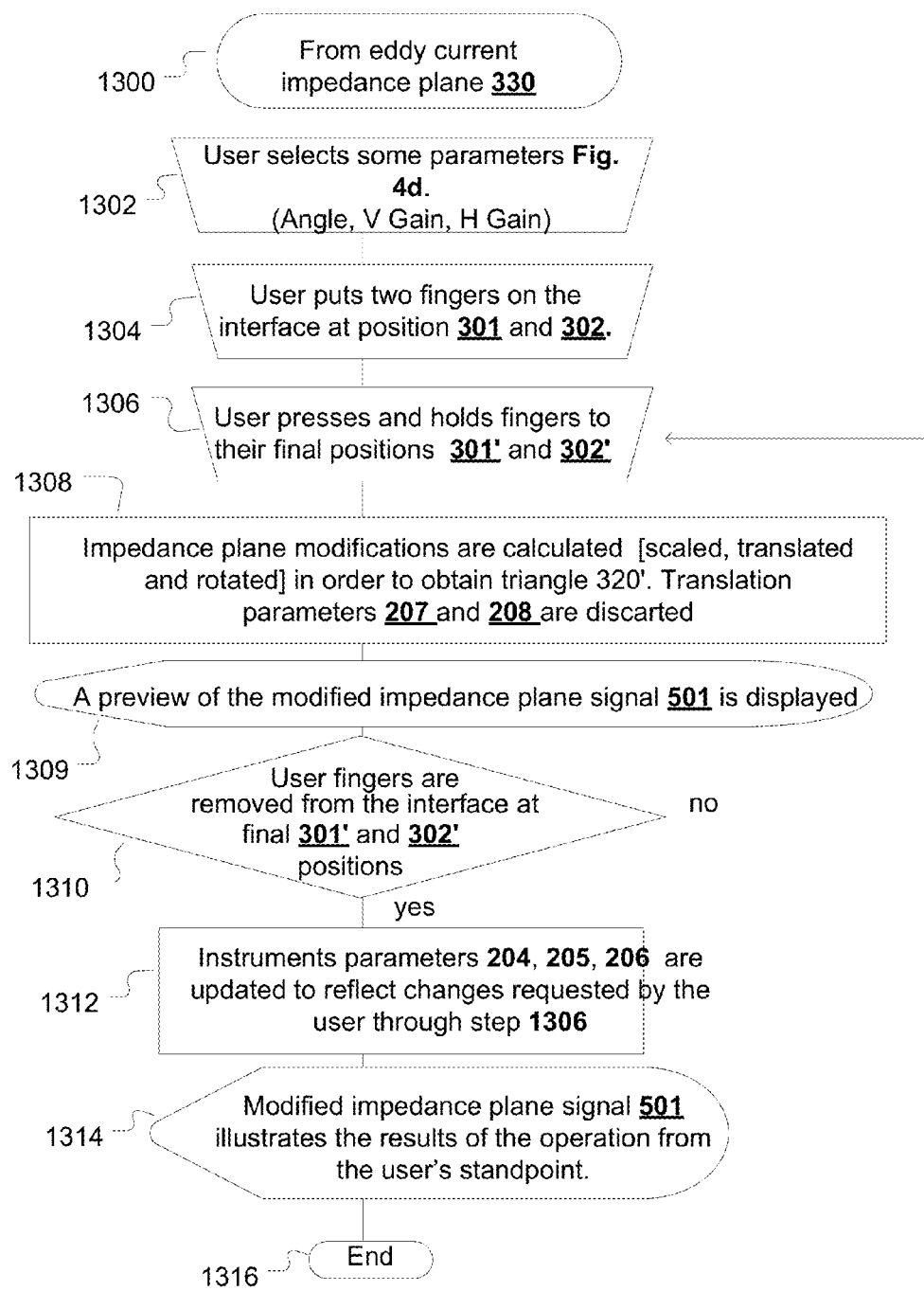
FIG. 10 is a flow diagram illustrating the operation illustrated in FIG. 5 according to an aspect of the invention.

When only a few parameters are selected, such as illustrated in FIG. 2a, FIG. 2b and FIG. 2d, calculations are essentially similar to those described in FIG. 8 and FIG. 9 except that only selected parameters are modified by the process. The example shown in FIG. 5 and FIG. 10 illustrates the behaviors of the system when touch screen operation 311 is made on impedance plane 330 with parameter selection illustrated on FIG. 2d to provide an impedance plane 501. In this case the translation parameters 207 and 208 are discarded step 1308.

Figure 6A:
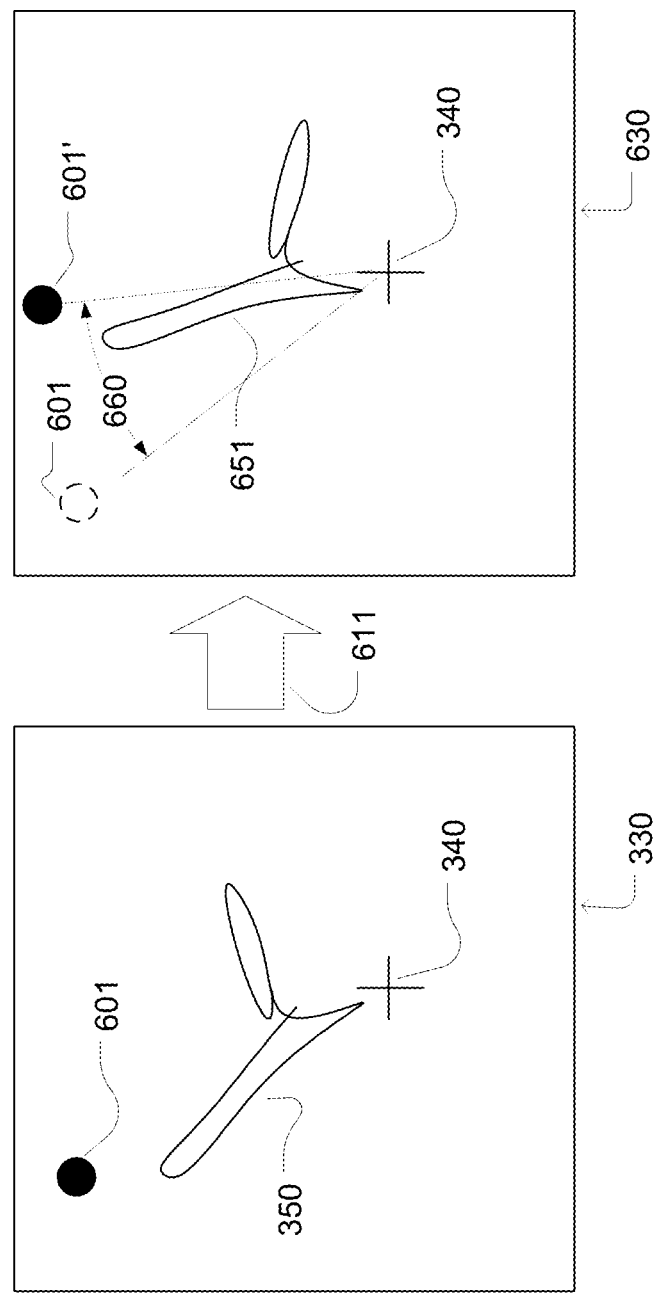
FIG. 6 illustrates various single contact operations possible according to an aspect of the invention.
Figure 6B:
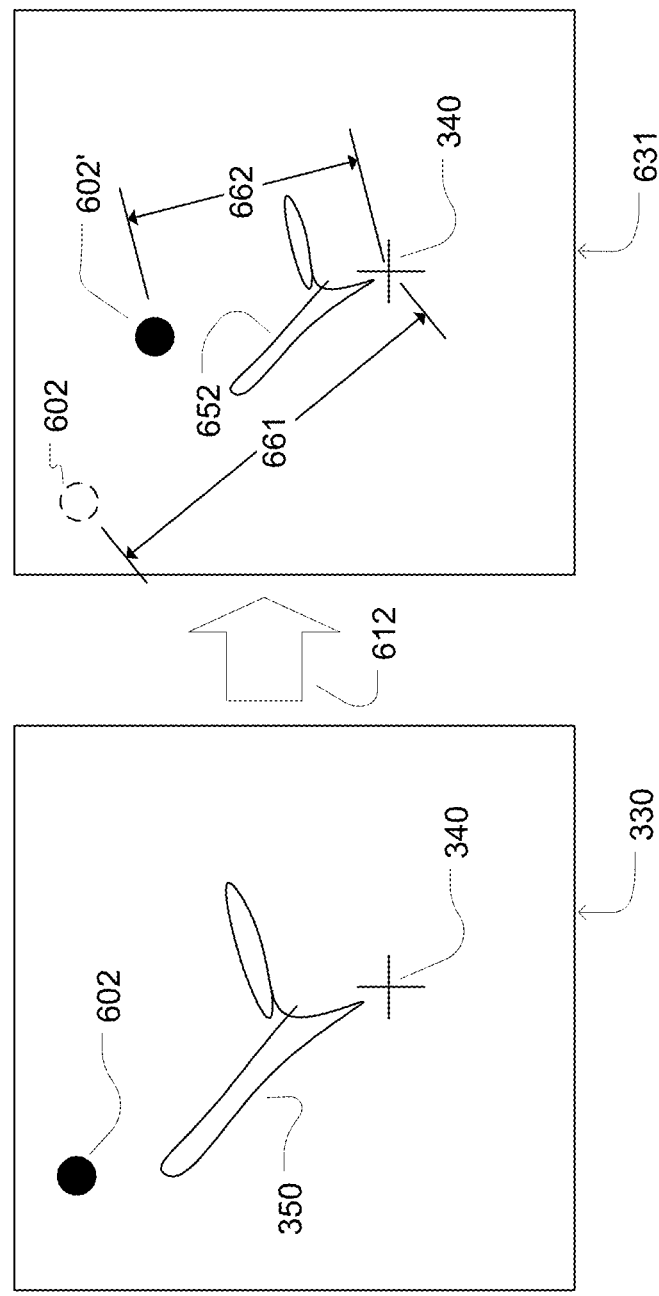
Figure 11:
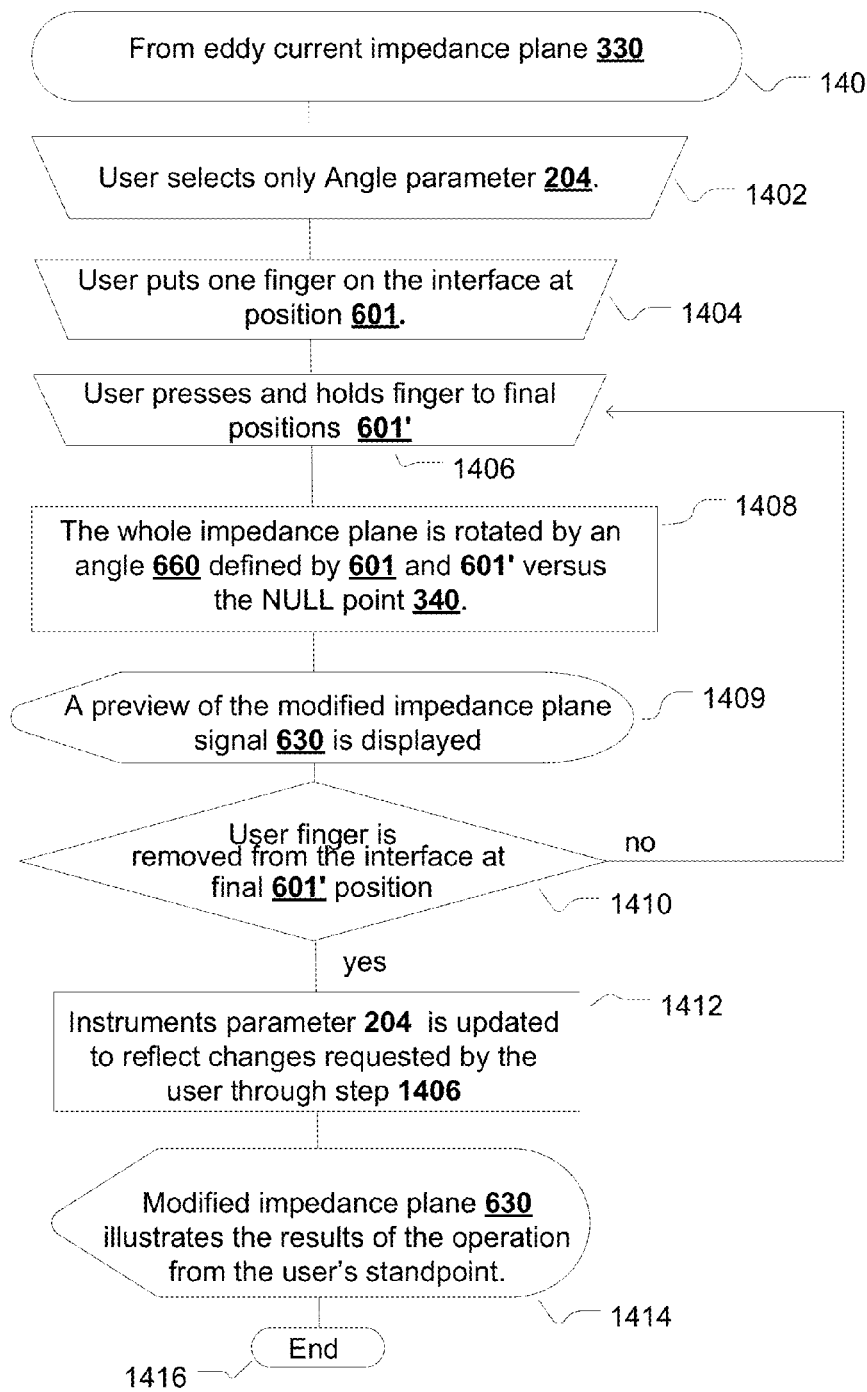
FIG. 11 is a flow diagram illustrating the operation previously illustrated on FIG. 6 according to an aspect of the invention.
Figure 12:
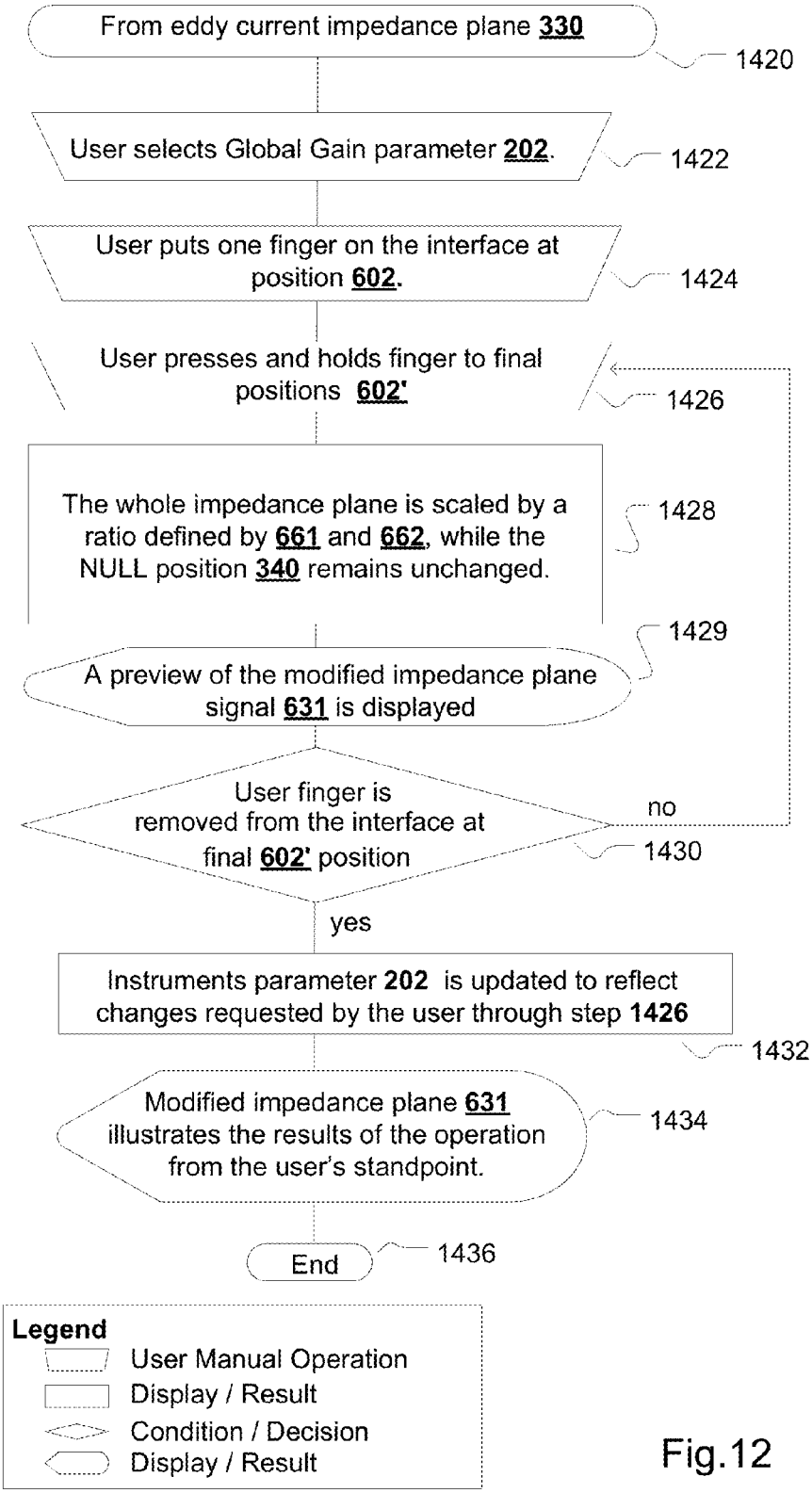
FIG. 12 is a flow diagram describing the operation previously illustrated on FIG. 6b according to an aspect of the invention.
Figure 13:
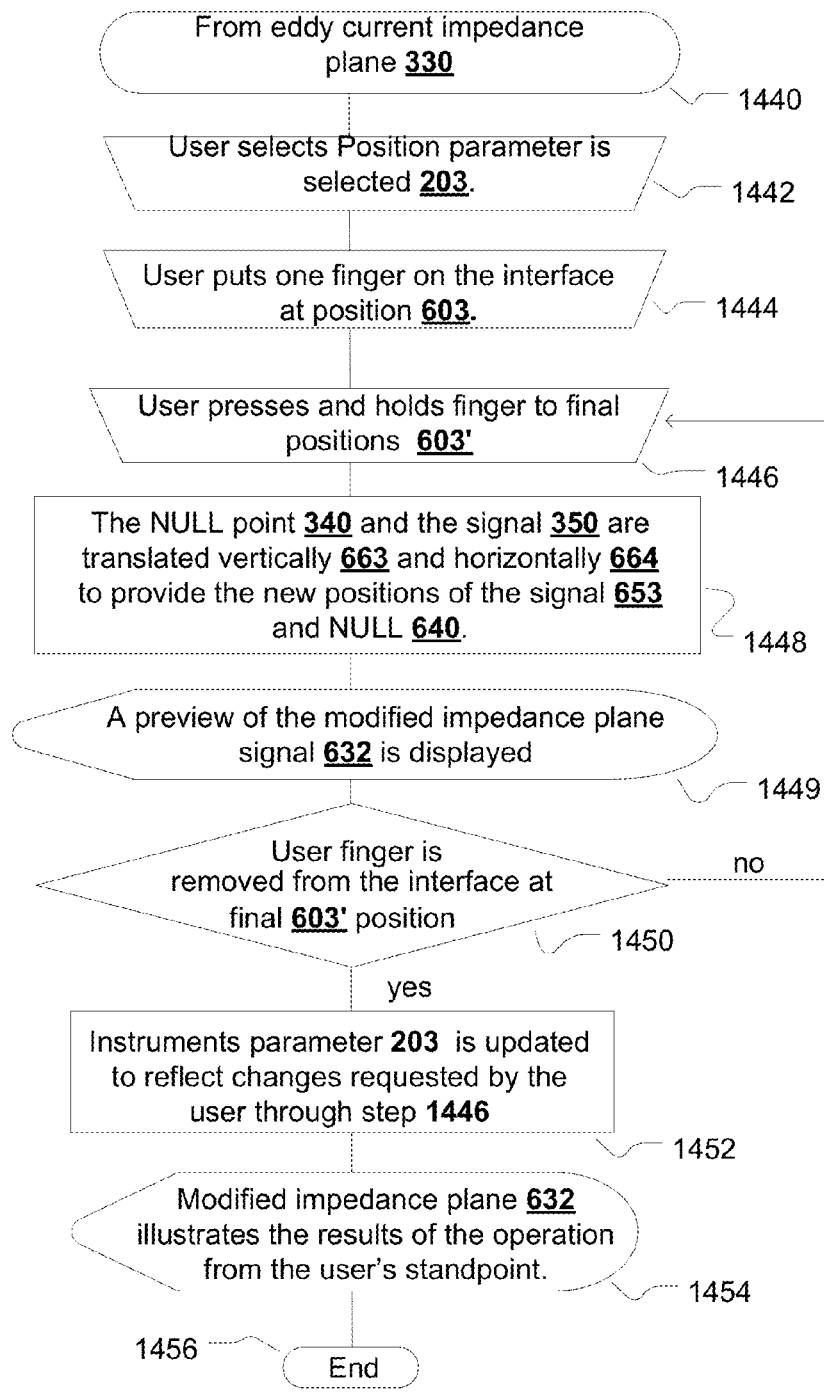
FIG. 13 is a flow diagram describing the operation previously illustrated on FIG. 6c according to an aspect of the invention.

In addition to the previously described two contact operation, it is possible to manipulate the impedance plane with a single contact in some situations. For example, as illustrated on FIG. 6a and FIG. 11, if the angle 204 is the only selected parameter (step 1402) when contact 601 is moved toward its final position 601' (step 1406), the impedance plane will be rotated by an angle 660 defined by the 601 and 601' versus null point 340 (step 1408). FIG. 6b and FIG. 12 illustrate the situation in which gain 202 is selected (step 1422). In this case signal 350 is scaled by the ratio defined by 661 and 662 (step 1428), while the null position 340 remains unchanged. It is of course possible to affect only vertical gain 206 or horizontal gain 205 with the same method. Another possibility shown in FIG. 6c and FIG. 13 shows the effects of single contact movement when position 203 is selected (step 1442). In this case, null point 340 and signal 350 are translated vertically 663 and horizontally 664 to provide the new positions of the signal 653 and null 640 (step 1448) on the impedance plane 632. It is of course possible to affect only the vertical position 208 or horizontal position 207 with the same method.

Some parameters, such as position and gain, can also have a limited range of variability. Typically, the null position will be kept within the impedance plane display; the gain can also be limited to reflect some limitation of the test equipment. In this case, the operation described in FIGS. 8-11 can be limited according to these predefined parameter's range.

Figure 7:
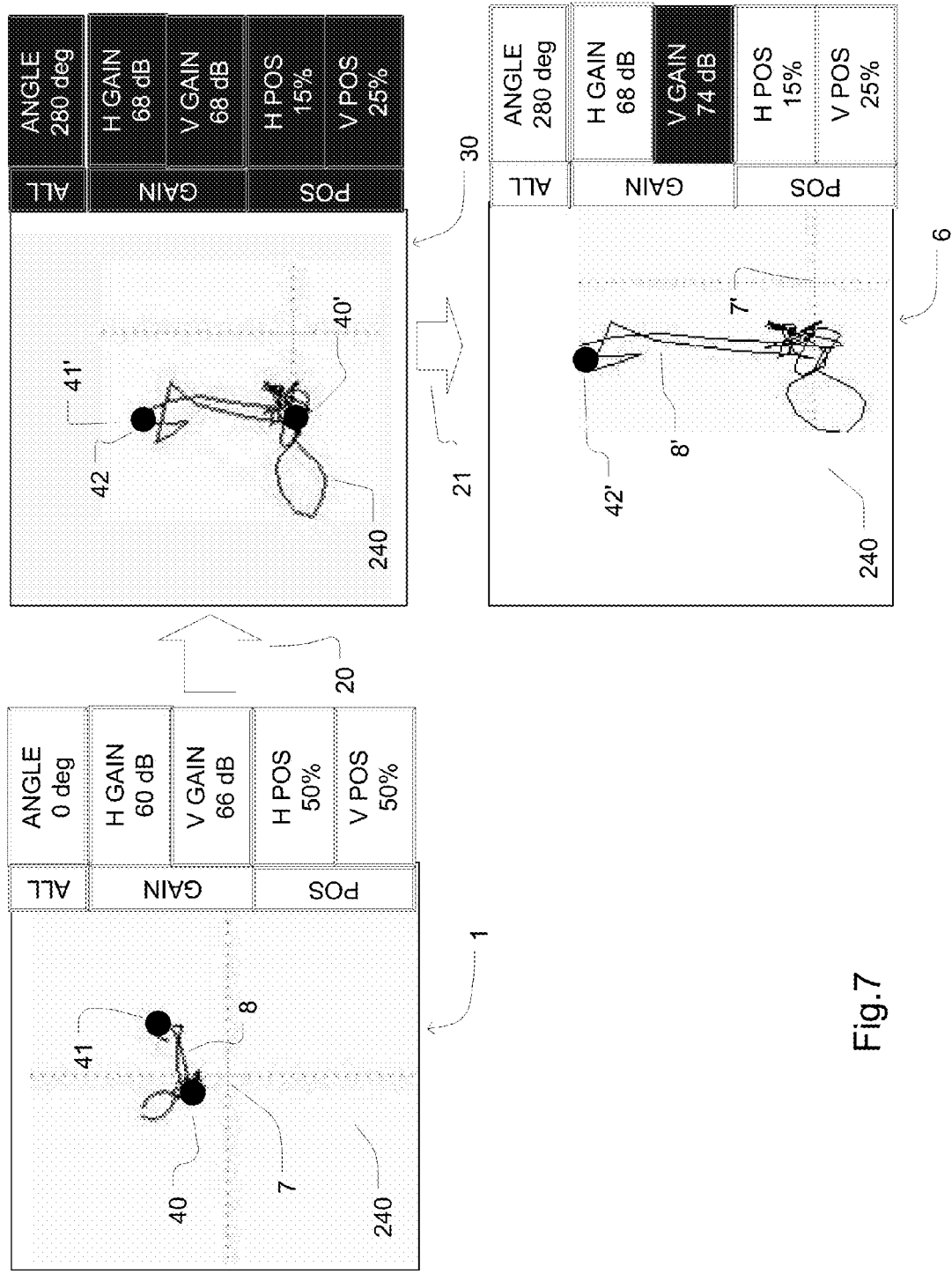
FIG. 7 illustrates how a five step sequence of prior art methods may be performed with two steps according to an aspect of the invention.

Now looking at FIG. 7, we see how results equivalent to a prior art process can be achieved with only two operations 20 and 21 using the touch screen based method of the invention while the prior art process requires at least the five following steps: gain modification, signal rotation, vertical gain modification, vertical position translation and horizontal position translation. The first operation 20 combines signal rotation, Gain and null position translation (horizontal and vertical) using a two point contact on the touch screen interface 240. The second operation 21 involves a modification limited to the vertical gain using only a single point contact on the touch screen interface 240.

The teaching of the invention also applies for eddy current test instruments capable of handling more than one test signal (for example with dual frequency testing or multi-channel instruments). In this case, the instrument should provide the ability to select one impedance plane signal at a time in order to conduct the manipulations.

The method to render the impedance plane preview (steps 1109, 1213, 1309, 1409, 1429 and 1449) is dependant on the processing capabilities of the test instrument. An instrument with sufficient processing capabilities will render the full impedance plane manipulation in real time to provide the user with a full feedback of the signal resulting from the process. A more limited instrument could provide feedback on a few important signals such as peaks, NULL position, etc. Indications showing the locations of the contact on the touch screen could also be useful to conduct the manipulation.

Impedance plane manipulations with the touch screen approach described herein are possible when the acquisition is stopped (frozen data manipulation, as first discussed in paragraph 8) or when the acquisition is running. In the later case, it is proposed to freeze the display during the manipulation itself from the touch of the screen to the release of the contact (with a possible delay).

Although discussed with respect to a touch screen device, it would be understood that other types of displays that provide for user manipulation of an image using a mouse, a separate control pad, a trackball or track pad, a joystick, arrow directional controls, or other types of controls separate from or in addition to the touch screen, are also contemplated and could be readily substituted by a person of ordinary skill in the art within the spirit of the present invention. In addition, as would be readily understood, a user need not touch some types of touch screens to effect (touch) or input to the touch screen. That is, the user may hover over or merely point to portions of a touch screen and sensors will detect the user's hand or finger, including the direction, timing or other pattern thereof, and this movement of the user's hand or finger away from the touch screen would be accurately interpreted as interacting with or directing or controlling the displayed image on the screen.

Touch screens may use various types of display systems, including LEDs, LCDs, CRTs, OLED, displays or other types of electronic displays to convey electronic information or electronic image information to the user. The buttons 204-208 illustrated in FIG. 1 and FIGS. 2a-2d, may be implemented as soft buttons or may be provided as separate physical buttons adjacent to the touch screen 240. Although shown as a wired connection between probe 130 and instrument 200, it will be understood that other types of connection, including a wireless connection implemented via Bluetooth or other types of close or medium distance radial frequency or other frequency technology, including, for example, cellular or other types of wireless signaling, are also contemplated.

It must also be understood that impedance plane manipulation using the touch screen can apply on previously acquired impedance plane data 1511 and/or on live data (i.e. data to be acquired be the system). For live data, impedance plane manipulations can be limited to digital modifications or can effectively modify some analog setting (for example analog GAIN) in the instrument.

Other possible applications of the invention are bond testing instruments which also rely on the impedance plane for defect detection.

Although the present invention has been described in relation to particular embodiments thereof, many other variations, combinations of features and modifications and other uses will become apparent to those skilled in the art. It is preferred, therefore, that the present invention be limited not by the specific disclosure herein, but only by the appended claims.

What is claimed is:

1. A system for enabling manipulation by a user of an impedance plane of a non-destructive testing device, the impedance plane is displayed on a touch screen of the device based on impedance plane data and the touch screen is configured for displaying test result and receiving touch-input from the user, the system comprising:
    an impedance plane data processing module configured to provide to a touch screen rendering module with a first set and a second set of the impedance plane data including at least a majority of parameters comprising: angle, horizontal gain, vertical gain, horizontal null point position, and vertical null point position;
    a touch screen user selection module configured to sense which one of the at least one of the parameters is being selected as a selected parameter according to a selection touch by the user;
    the touch screen rendering module configured to render a first image and a second image representing a first set of impedance plane data and a second set of impedance plane data, respectively, with respective test result;

wherein the change from the first image to the second image representing at least one of re-positioning, re-scaling and re-translating of the impedance plane is provided by the impedance plane data processing module based on a manipulation move of user's touch on the touch screen for the selected parameter.

2. The system of claim 1, wherein the manipulation move operated on the selected parameter is a multi-point touch on the touch screen as a single, continuous and simultaneous operation by at least two fingers of the user.

3. The system of claim 2, wherein the manipulation move is a sliding move of at least two fingers pressed against the touch screen.

4. The system of claim 3, wherein the touch screen rendering module is configured to redraw the second impedance image based on the second position of the two fingers.

5. The system of claim 2, wherein the manipulation move starts with a first position of the two fingers corresponding to the first set of the impedance plane data, ends with at a second position of two fingers corresponding to the second set of the impedance plane data.

6. The system of claim 1 further comprising areas of the touch screen as virtual buttons displayed on the touch screen, wherein the selected parameter is via the selection touch upon one of the virtual buttons displayed on the touch screen.

7. The system of claim 1, wherein the system is configured to remove a gain difference between the horizontal gain and the vertical gain before rendering the second image of the impedance plane.

8. The system of claim 1, wherein the system is configured to respond to a subsequent touch of the user's hand at a time following the selection touch by a further redrawing comprising at least one of re-positioning, re-scaling and re-translating the image representing the same impedance plane signal.

9. The system of claim 1, wherein the system is configured to provide controls to facilitate the user selecting one or more of the parameters by designating a parameter of the parameters; and,
the system is configured to interpret the selection touch by the user's hand based on the designating.

10. The system of claim 1, further comprising a storage module configured to store data generated by the non-destructive testing device,
wherein the impedance plane data processing module is configured to receive the parameter values from the storage module configured to store data generated earlier by the non-destructive testing equipment.

11. The system of claim 1, wherein the impedance plane data processing module is configured to generate the parameter values based on data received from the non-destructive testing equipment in real time.

12. The system of claim 1, wherein the first and the second set of impedance plane data can be all sourced from a same set of impedance signal obtained as part of the test result.

13. A method of enabling the manipulation by user of an impedance plane
generated by a non-destructive testing device, the impedance plane is displayed on a touch screen of the device based on impedance plane data and the touch screen is configured for displaying test result and receiving touch-input from the user, the method comprising:
receiving a first set of the impedance plane data associated with a first position of at least two fingers, the data including at least a majority of parameters comprising: angle, horizontal gain, vertical gain, horizontal null point position, and vertical null point position;
selecting at least one of the parameters as a selected parameter by applying a selection touch on the touch screen;
applying a manipulation move of the at least two touch points to a second position of the at least two touch points, the manipulation move representing at least one of move of re-positioning, rescaling and re-translating of the impedance plane for the selected parameter;
redrawing the image of a second impedance plane according to a second set of impedance plane data represented by the second position of the at least two touch points.

14. The method of claim 13, the manipulation move is a multi-point touch on the touch screen as a single, continuous and simultaneous touch by at least two fingers of the user.

15. The method of claim 13, wherein the manipulation move is a sliding move of at least two fingers pressed against the touch screen.

16. The method of claim 13, further comprising removing a gain difference between the horizontal gain and the vertical gain before the re-drawing of the impedance plane image.

17. The method of claim 16, further comprising automatically providing areas of the touch screen as virtual buttons displayed on the touch screen,
wherein the designating the at least one parameter is via the selection of the virtual buttons displayed on the touch screen.

18. The method of claim 13, further comprising detecting a subsequent touch of the user's hand at a time following the selection touch; and
automatically further re-drawing by at least one of re-positioning, re-scaling and re-translating the re-drawn image a second time, the re-drawn second image representing the same impedance plane signal.

19. The method of claim 13, further comprising:
automatically providing controls on the touch pad to facilitate the user selecting at least one parameter of the parameters by designating the at least one parameter; and
interpreting the selection touch by the user's hand in accordance with the designating of the at least one parameter by the user.

20. The method of claim 13, further comprising rendering a triangle on the touch pad at the first image, wherein one vertex of the triangle represents the null point.

21. The method of claim 13, wherein the impedance plane signal is received from a database storing data, and the method further comprises the impedance plane signal from the non-destructive testing equipment to the database.

22. The method of claim 13, wherein the impedance plane data is received in real-time from the non-destructive testing device.

* * * * *